US012715965B2

(12) United States Patent
Krzykawski et al.

(10) Patent No.: US 12,715,965 B2
(45) Date of Patent: Aug. 25, 2026

(54) PROTEIN HYDROGEL, PREPARATION METHOD AND USE THEREOF

(71) Applicant: REAL RESEARCH SP. Z O.O., Cracow (PL)

(72) Inventors: Marcin Przemysław Krzykawski, Targanice (PL); Renata Krzykawska, Targanice (PL)

(73) Assignee: REAL RESEARCH SP. Z O.O., Cracow (PL)

( * ) Notice: Subject to any disclaimer, the term of this patent is extended or adjusted under 35 U.S.C. 154(b) by 865 days.

(21) Appl. No.: 17/428,541

(22) PCT Filed: Feb. 4, 2020

(86) PCT No.: PCT/IB2020/050867
§ 371 (c)(1),
(2) Date: Aug. 4, 2021

(87) PCT Pub. No.: WO2020/161613
PCT Pub. Date: Aug. 13, 2020

(65) Prior Publication Data

US 2022/0135749 A1 May 5, 2022

(30) Foreign Application Priority Data

Feb. 4, 2019 (EP) .................................... 19460008

(51) Int. Cl.

| | |
|---|---|
| ***C08J 3/075*** | (2006.01) |
| ***C08H 1/02*** | (2006.01) |
| ***C08H 1/06*** | (2006.01) |
| ***C08J 3/24*** | (2006.01) |
| ***C08L 89/06*** | (2006.01) |
| ***C12N 5/071*** | (2010.01) |

(52) U.S. Cl.
CPC ................ *C08J 3/075* (2013.01); *C08H 1/02* (2013.01); *C08H 1/06* (2013.01); *C08J 3/24* (2013.01); *C08L 89/06* (2013.01); *C12N 5/069* (2013.01); *C08J 2389/06* (2013.01); *C12N 2503/00* (2013.01); *C12N 2513/00* (2013.01); *C12N 2533/54* (2013.01)

(58) Field of Classification Search
CPC .... C08J 3/075; C08J 3/24; C08H 1/02; C08L 89/06; C12N 2533/54
See application file for complete search history.

(56) References Cited

FOREIGN PATENT DOCUMENTS

| | | | | |
|---|---|---|---|---|
| WO | 02090528 A1 | | 11/2002 | |
| WO | 2008016983 A1 | | 2/2008 | |
| WO | WO-2008016983 A2 | * | 2/2008 | ........... A61K 38/363 |

OTHER PUBLICATIONS

Usta, M. et al. Biomaterials 24 (2003) 165-172. (Year: 2003).*
Oberleithner, H., et al. Hypertension. 2004, 43, 5, pp. 952-956. (Year: 2004).*
Nwe N., et al. Process Biochemistry. 45, ,2010, 457-466. (Year: 2010).*
Zhao, X. et al. Adv. Healthcare Mater. 2016, 5, 108-118. (Year: 2016).*
Mad-Ali, S., et al. J. Food Sci. Technol. 2017, 54(6):1646-1654. (Year: 2017).*
Lab Pro Inc. Lab Refrigerators vs. Freezers: Which is Right for Your Lab? LinkedIn. Web. (Year: 2023).*
Sisson, K., et al. Biomacromolecules. 2009, vol. 10, No. 7. (Year: 2009).*
Lai, J. J. Mater. Sci: Mater. Med. 2010, 21:1899-1911. (Year: 2010).*
International Search Report issued in connection with PCT Application No. PCT/IB2020/050867 dated May 7, 2020.
Nwe N Et al., "Selection of a biopolymer based on attachment, morphology and proliferation of fibroblast NIH/3T3 cells for the development of a biodegradable tissue regeneration template: Alginate, bacterial cellulose and gelatin," Process Biochemistry, Elsevier Ltd., GB, vol. 45, No. 4, Apr. 1, 2010, pp. 457-466.

* cited by examiner

*Primary Examiner* — Andrea Olson
*Assistant Examiner* — Samuel L Galster
(74) *Attorney, Agent, or Firm* — Dennemeyer & Associates LLC

(57) ABSTRACT

The invention relates to a new protein hydrogel created on the basis of low-concentrated components: reagents A and B, the method of hydrogel preparation and its use.

11 Claims, 2 Drawing Sheets

PROTEIN HYDROGEL, PREPARATION METHOD AND USE THEREOF

CROSS-REFERENCE TO RELATED APPLICATIONS

This is a 35 U.S.C. 371 National Stage Patent Application of International Application No. PCT/IB2020/050867, filed Feb. 4, 2020, which claims priority to European application 19460008.6, filed Feb. 4, 2019, each of which is hereby incorporated by reference in its entirety.

BACKGROUND OF THE INVENTION

The invention relates to a protein hydrogel, the method of its preparation and its use for cell cultures, including 2D and 3D cell cultures, of both healthy and neoplastic cells, of both cell lines and primary cells; use for migration and invasion assays in a hydrogel in 3D conditions, performing angiogenesis assays and performing aortic sprouting assays.

There are now many different types of media for cell cultures in a three-dimensional environment. They can generally be divided into several types: protein hydrogels, synthetic hydrogels, scaffolds, hanging drop method etc.

The advantage of protein hydrogels is that they are the closest to the physiological environment for cell growth. Currently, the most frequently used material for cell cultures in three-dimensional conditions is a hydrogel, whose composition is made up of extracellular matrix (ECM) proteins. Other hydrogels produced inter alia from synthesised peptides are also available, but they are much less commonly used. On the other hand, collagen and gelatin are used to coat culture surfaces in two-dimensional cell cultures.

Collagen is also used for three-dimensional cultures. Typically, hydrogels cross-linked with a pH change are used. At low pH, collagen, e.g. a rat tail collagen, is dissolved, and after a culture medium of a more neutral pH is added to it, the collagen gelifies and cultures can be grown on it. Gelatin is a product of a partial hydrolysis of collagen fibres. Of the available gelatin kinds, two basic types can be identified, namely the acidic type, i.e. the one whose hydrolysis is carried out in an acidic environment, and the alkaline type, i.e. the one whose hydrolysis is carried out in an alkaline environment. Depending on the value determining the strength of gelification, gelatins of different Bloom values are identified. The higher the Bloom value, the greater the strength of gelification.

Currently, hydrogels that enable 3D cell cultures and angiogenesis assays are commercially available. One of a few examples of products that makes it possible to perform an angiogenesis assay is Matrigel® (and its derivatives). The main components of Matrigel are laminins, type IV collagen, proteoglycan, entactin and growth factors, extracted from the murine neoplasm, being Engelbreth-Holm-Swarm (EHS) sarcoma. U.S. Pat. No. 4,829,000 discloses compositions for cell cultures and a method for the production of a biologically active extract. It is also known from Orci et al., *Vascular outgrowths from tissue explants embedded in fibrin or collagen gels: a simple in vitro model of angiogenesis*, Cell Biology International Reports, Vol. 9, No. 10, October 1985, to use collagen for performing an angiogenesis assay, but the use of collagen is described in the prior art as labour-intensive and giving poorly reproducible results. Hydrogels whose basic building material is gelatin, and specifically methacrylated gelatin (FastLink GelMA), are also commercially available, an exemplary producer of such a hydrogel being Stemorgan Inc. These hydrogels, however, use gelatin of a concentration of about 10%, which significantly exceeds the gelatin concentration range proposed in this invention. Additionally, the gelatin in GelMA is cross-linked with an initiator producing free radicals under the influence of UV radiation.

The object of the invention is to provide a hydrogel based on low-concentrated mixtures which will solve the existing problems known from the prior art and will be less toxic, while reducing production costs and increasing production efficiency. Because of the components used, the new hydrogel gives significantly greater reproducibility as compared to the hydrogels known from the prior art. This reproducibility results from two fundamental features of the new hydrogel. First of all, as compared to the hydrogels known from the prior art, the new hydrogel is substantially free of growth factors, which stems from two reasons: firstly, gelatin production technology drastically lowers the survival potential of growth factors, and secondly, during gelatin cross-linking reaction with glutaraldehyde (GTA), possible residual amounts of growth factors are inactivated. The second grounds for the reproducibility of the new hydrogel is the reproducibility of the concentrations of its components.

In the prior art, it is known from DOILLON et al. *Three-dimensional Culture System as a Model for Studying Cancer Cell Invasion Capacity and Anticancer Drug Sensitivity*, Anticancer Research 24: 2169-2178 (2004), to use collagen with a fibrin addition as a component for a 3D model of neoplastic cell cultures. In addition, from Yamada & Even-Ram: Cell migration in 3D matrix 2005, the use of 3D cell cultures is known, the use based on collagen and fibrin to test the potential of neoplastic cells to invade and migrate inside the hydrogel.

In the prior art, from MONTESANO et al., *Vascular outgrowths from tissue explants embedded in fibrin or collagen gels: a simple in vitro model of angiogenesis*, Cell Biology International Reports, Vol. 9, No. 10, October 1985, the use of 3D endothelial cell cultures is also known, the use based on collagen and fibrin and making it possible to perform an angiogenesis assay. These hydrogels, however, do not contain GTA.

GTA (glutaraldehyde) is one of the most frequently used chemical cross-linking agents, particularly because of its highly-effective stabilisation of collagen materials, by the reaction of free amino groups of lysine or amino acid residues of hydroxy-lysine of polypeptide chains with aldehyde groups. However, in the context of cell cultures, its disadvantage is toxicity even at very low concentrations. As disclosed in Ou&Yang *The micro patterning of glutaraldehyde (GA)-crosslinked gelatin and its application to cell-culture*, Lab on a Chip, 2005, there were attempts to dissolve this problem by washing hydrogel with water in order to remove the residues after wetting in 45% GTA, but even after an additional rinsing step, the GTA concentrations used were so high that the hydrogels produced according to the disclosed method have different qualities than the hydrogels of the invention.

In contrast, Bigi et al., *Mechanical and thermal properties of gelatin films at different degrees of glutaraldehyde cross-linking*, Biomaterials 22 (2001) 763-768, show that hydrogel compositions containing a GTA-cross-linked gelatine are characterised by good stability. According to the results presented in the range from 0.1% to 1% GTA, the extent of cross-linking increases from 60% to 100% and thermal and mechanical properties differ accordingly, which is why it is possible to employ different GTA concentrations to modulate the physicochemical properties of the film. However, GTA concentration is still high enough to disable a cell culture on hydrogels prepared in this manner.

Document CN105316285 discloses a method for the production of media for a 3D cell culture, which method comprises dissolving collagen in acetic acid, dissolving chitosan in acetic acid, mixing them, drying and then adding GTA and allowing to stand for 8-16 h for cross-linking and purifying the obtained hydrogel.

There are no hydrogels in the prior art now that are created by cross-linking of proteins by low concentrations of GTA. By reducing the concentration and at the same time by reducing the proportion of GTA to the amount of lysine that can be bound, hydrogels were obtained of better physico-chemical qualities as well as of lower toxicity, which made it possible to use the hydrogels of the invention for 2D and 3D cell cultures, of both healthy and neoplastic cells, migration and invasion assays in a hydrogel in 3D conditions, performing angiogenesis assays or performing aortic sprouting assays.

However, there is still a need to develop a hydrogel of precisely selected qualities, such as e.g. density, hardness and elasticity, which in this way will be able to be widely used in tests, e.g. for performing angiogenesis assays. In the present invention, the precise selection of density and hardness parameters takes place suitably by modification of gelatin or collagen and GTA concentrations. Elasticity is the result of the two above parameters being modified and the hydrogel production method. The level of cross-linking determines the parameters of the final product and only the technology described by the inventors makes it possible to lower the concentrations to levels low enough to be able to obtain parameters of the hydrogels of the invention.

Another object of the invention is to provide a hydrogel for the use in performing angiogenesis assays (angiogenesis assay, in vitro angiogenesis tube formation assay, endothelial cell tube formation assay). The new hydrogel is also used in other cell cultures, such as for example neoplastic cell cultures, in lab-on-a-chip cultures, plant and bacterial cell cultures and flow cultures.

An additional technical problem solved by this invention is the elimination of toxicity, which remains after the reaction of GTA with gelatine. With the removal of the amounts of GTA used in the invention, them already being residual, the produced hydrogel makes it possible for even the most sensitive cells to grow.

Additionally, an extremely important feature of the invention is the economic aspect. Firstly, it is possible to react GTA with gelatin so that at such low concentrations hydrogel can be created. Additionally, the relatively inexpensive reagents used in the invention significantly reduce the cost, while at the same time increasing the efficiency and cost-effectiveness of the production, with it being possible for the claimed product to function on a much larger scale.

An extremely important aspect is the fact that the protein hydrogel created in such a manner is a far more reproducible product for cell cultures than the products with a similar range of applications being commercially available today. The protein hydrogel of the invention is the only product of this class which is free of growth factors and is also of a significantly increased product reproducibility. It is substantially free or free of growth factors since the manufacturing of each of commercially available components inactivates the residual growth factors which could be present in them and additionally, the growth factors are inactivated during the reaction with GTA. The high reproducibility of the inventive protein hydrogel alone derives from the fact that it is synthesised from commercially available components, whereby their concentrations can be very precisely selected and controlled in the final product.

The subject matter of the invention is a protein hydrogel comprising: reagent A, being gelatin or collagen, reagent B, being a cross-linking agent, being GTA (glutaraldehyde) and solvent, characterised in that reagent A is present in the final concentration from 0.15% wt. to 1.5% wt., with a ratio of reagent A to reagent B of 0.375-4.5 mg to 0.01-0.15 mg in one portion of the hydrogel.

Preferably, the final concentration of reagent A is from 0.25% wt. to 1% wt., with a ratio of reagent A to reagent B of 0.625-3 mg to 0.0135-0.075 mg in one portion of the hydrogel.

Particularly preferably, the final concentration of reagent A is from 0.3% wt. to 0.8% wt., with a ratio of reagent A to reagent B of 0.75-2.4 mg to 0.021-0.045 mg in one portion of the hydrogel.

Preferably, the protein hydrogel of the invention is characterised in that gelatin is gelatin of the Bloom value of at least 225, preferably of the Bloom value of 300.

Preferably, the protein hydrogel of the invention is characterised in that the solvent is an aqueous solution, more preferably is selected from the group: $dH_2O$, PBS, HBSS and most preferably is PBS.

Another subject matter of the invention is the method of producing a protein hydrogel of the invention, comprising the steps of:

a) addition a suitable amount of reagent A, being gelatin or collagen, in an aqueous solution, preferably selected from the group: $dH_2O$, PBS, HBSS and most preferably PBS;
b) heating up the mixture of step a) to dissolve the gel;
c) optionally, initially stabilising the gel;
d) preparing reagent B, being a cross-linking agent, being GTA, by dissolving it in an aqueous solution and cooling it;
e) adding reagent B, as prepared in step d), to the gel prepared in step c);
f) optionally mixing the obtained mixture;
g) cross-linking;
h) optionally purifying the hydrogel of an excess of reagent B, characterised in that reagent A is present in the final concentration from 0.15% wt. to 1.5% wt., with a ratio of reagent A to reagent B of 0.375-4.5 mg to 0.01-0.15 mg in one portion of the hydrogel, the initial stabilisation of the gel takes place when the gel reaches the temperature 0-12° C. and its duration is at least about 5 minutes; steps d)-g) are performed at reduced temperature from about 0° C. to about 12° C., in step g) the duration of cross-linking is at least 12 h.

The addition of reagent B, as prepared in step d), to the gel prepared in step c) may take place by adding reagent B to the gel or adding reagent B onto an already gelified gel.

Preferably, the final concentration of reagent A is from 0.25% wt. to 1% wt., with a ratio of reagent A to reagent B of 0.625-3 mg to 0.0135-0.075 mg in one portion of the hydrogel.

Particularly preferably, the concentration of reagent A is from 0.3% wt. to 0.8% wt., with a ratio of reagent A to reagent B of 0.75-2.4 mg to 0.021-0.045 mg in one portion of the hydrogel.

Preferably, the duration of initial stabilisation is 30 minutes to 48 hours, most preferably 45 minutes to 24 hours.

Preferably, the duration of cross-linking is above 48 hours, most preferably above 72 hours.

If the purification of the hydrogel in step h) takes place, it preferably takes place by means of rinsing with an aqueous solution, preferably an aqueous solution for cell cultures, preferably PBS, or by means of neutralising reagent B, preferably by adding L-lysine.

The optional purification of the hydrogel of the excess of reagent B in the above described step h) of the method takes place by means of every substance capable of reacting with and inactivating —CHO groups. An example of such a substance is L-lysine, but also proteins comprising unbound side chains —$NH_2$ of lysine. This substance is used in order to neutralise the toxic cross-linking substance, being for example GTA comprising two —CHO groups. This substance is used in concentrations being multiplications of molar concentrations of —CHO groups added when the hydrogel is produced. For example, when 30 μl of 0.1% GTA is used, about $0.6*10^{-3}$ moles of —CHO groups is then present in such a volume. Using a 10× (ten times) concentration of L-lysine means that 10 times more moles of L-lysine is added than —CHO groups have been added to produce the hydrogel. L-lysine comprises only one —$NH_2$ group in the side chain, said group being able to bind —CHO group, and is typically added in the volume equal to the initial volume of the hydrogel.

Another subject matter of the invention is the use of the protein hydrogel of the invention for cell cultures, preferably for 3D cell cultures.

Yet another subject matter of the invention is the use of the protein hydrogel produced by the method of the invention to perform an angiogenesis assay, with the duration of the initial stabilisation in step c) being from 10 to 90 minutes, preferably from 15 to 60 minutes, most preferably from 40 to 55 minutes, and the duration of the cross-linking being above 60 hours, and the final concentration of reagent A being 0.35-0.55%, with such a proportion being maintained in one portion of the hydrogel that for the mass of reagent A in the range from 0.875 mg to 1.375 mg falls from 0.024 mg to 0.036 mg of reagent B.

Preferably, such a proportion is maintained in one portion of the hydrogel that for the mass of reagent A in the range from 1 mg to 1.25 mg falls from 0.027 mg to 0.033 mg of reagent B.

Particularly preferably, such a proportion is maintained in one portion of the hydrogel that for the mass of reagent A in the amount of 1 mg falls 0.03 mg of reagent B.

The lowering of the concentrations of GTA to a value below 0.15 mg (i.e. 0.5% in 30 μl or 0.05% in 300 μl), GTA being added to gelatin (i.e. to 250 μl or to 300 μl, respectively) of a concentration of 0.15%-1.5%, not only reduces its toxicity (which is then easier to be removed), but, most importantly, makes it possible to modify the elasticity and viscosity of the hydrogel and thus affects the parameters of cell growth and offers completely new opportunities.

The terms used herein have the meanings generally accepted in the art.

The term "reduced temperature" means the temperature within the range of about 0° C. to about 12° C., preferably about 0° C. to about 8° C., particularly preferably on ice, with the expression being able to be used interchangeably with the expression "fridge temperature".

The term "about" is intended to indicate that the given numerical values have defined values, which, however, may be subject to an error of 10%.

The term "aqueous solution" preferably means an aqueous solution for cell cultures, preferably selected from the group: $dH_2O$, PBS, HBSS, particularly preferably PBS.

The term "cross-linking agent", "reagent B", means a chemical compound that performs a function of linking two or more protein chains. Protein chains are linked by amino acid side chains or amino acids at the termini of proteins. The linking of proteins is called cross-linking when as a result of protein chains being linked a network of proteins is created, also called a hydrogel. As shown in the examples in the work by Sung et al. *Evaluation of gelatin hydrogel crosslinked with various crosslinking agents as bioadhesives: In vitro study*, Journal of biomedical materials Research, 1999, where exemplary protein cross-linking mechanisms are listed, protein cross-linking may occur, for instance, by —$NH_2$ or —COOH functional groups. As disclosed in Bigi et al., the cross-linking agent is preferably pentane-1,5-dial (glutaraldehyde, GTA). GTA cross-links gelatin or collagen by covalently binding —$NH_2$ groups between proteins and additionally, by binding those groups inside one protein, thus stabilising them.

The term "protein hydrogel portion/well" means an exemplary portion, during the creation of which the proportions given in the claims were respected. Two examples of "portions" were used, 250 μl of gel, to which 30 μl GTA is added (to the inside of the gel, as a result of which the target volume is 280 μl of hydrogel). Another example of a portion is 300 μl gel portion, onto the surface of which 300 μl GTA is added—here the portion is limited to 300 μl of hydrogel, since GTA added onto the surface of the gel does not mix with the gel itself and thus does not increase the volume of the finally resulting hydrogel. Reagent B applied is such a manner diffuses into the gel, where the cross-linking reaction takes place, and the remaining excess is removed by suction from the surface of the hydrogel. For the purposes of the present invention hydrogel portion volumes given above and disclosed in the embodiments were presented. However, the protection also covers smaller and greater amounts of reagents A and B, with the proportions of reagent A to B, as described in the description, being respected.

"Reagent A" means gelatin or collagen, but also any other protein of the same or similar amino acid sequence as the one of gelatin or collagen, obtained from living organisms, as well as a recombinant protein, i.e. obtained by production in genetically modified organisms.

BRIEF DESCRIPTION OF THE DRAWINGS

The subject matter of the invention is shown in the embodiments and in the figures, where:

FIG. 2A shows 4T1 cells 14 days after seeding and FIG. 2B 17 days after seeding.

DETAILED DESCRIPTION

Figure 1:
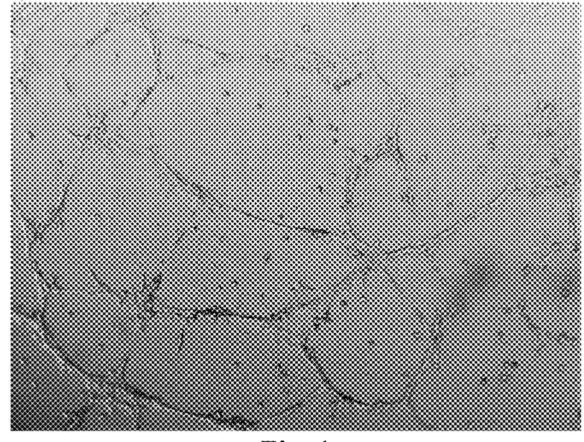
FIG. 1—shows tube-forming HUVEC endothelial cells on a hydrogel. This test is a model assay illustrating the formation of blood vessels. It enables pro- and anti-angiogenic tests.

Embodiments are shown below, them being only an illustration of the invention and not of a limiting nature.

Example I

Production of the Protein Hydrogel

To produce 60 hydrogel portions of a concentration of 0.4%, 0.06 g of type A Bloom 300 gelatin was weighed and dissolved in 14.94 ml of PBS solution. Each hydrogel portion contained 0.001 g of gelatin. The solution was heated at 37° C. to dissolve the gel and then sterilised by filtration. The gel prepared in this manner was pipetted into a 48-well plate at 250 μl per well and put into a fridge to cool and then stabilised for 45 minutes in the fridge. The remaining 12 gel portions remained unused. By taking 0.03 mg of GTA and supplementing to 30 μl of $dH_2O$, 0.1% GTA solution in $dH_2O$ was prepared earlier and cooled for 30 min in the fridge. To a cool, stabilised, but not gelified gel, 30 μl of GTA solution was added. GTA addition took place on ice. In each hydrogel portion, there was about 0.03 mg of GTA. Then the plate with the gel with GTA added was put to the fridge for 72 h. After that time, the resulting hydrogel was purified of excess GTA by hydrogel neutralisation, by adding L-lysine. L-lysine of a concentration 10× dissolved in PBS was used. The lysine was incubated with hydrogel for 24 h. The hydrogel prepared in this manner is ready for further use.

Example II

Production of the Protein Hydrogel

To produce 50 hydrogel portions of a concentration of 0.7%, 0.105 g of type A Bloom 300 gelatin was weighed and dissolved in 14.895 ml of PBS solution. Each hydrogel portion contained 0.0021 g of gelatin. The solution was heated at 37° C. to dissolve the gel and then sterilised by filtration. The gel was pipetted into a 48-well plate, 300 μl per well. The remaining 2 gel portions remained unused. The plate prepared in this manner was put to the fridge for 2 h. By taking 0.06 mg of GTA and supplementing to 300 μl of $dH_2O$, 0.02% GTA solution in $dH_2O$ was prepared earlier and cooled for minimum 30 min in the fridge. Onto the surfaces of the gelified gel, 300 μl of GTA solution was poured gently and put into the fridge for 24 h. GTA addition took place on ice. In each hydrogel portion, there was about 0.06 mg of GTA. After that time, the resulting hydrogel was purified of excess GTA by rinsing the hydrogel 3 times with PBS. The hydrogel prepared in this manner is ready for further use.

Example III

Onto the hydrogel prepared in Example I, endothelial (HUVEC) cells were seeded at density of 15 thousand cells/well of a 48-well plate (depending on the specific cell line batch and the number of cell divisions, the density of the seeded cells may vary from 5 to 50 thousand cells/well of a 48-well plate). The endothelial cells were cultured in EGM™-2 BulletKit™ Lonza medium. The result of the experience were tubes formed on the surface of the hydrogel by the endothelial cells (FIG. 1).

Example IV

Figure 2:
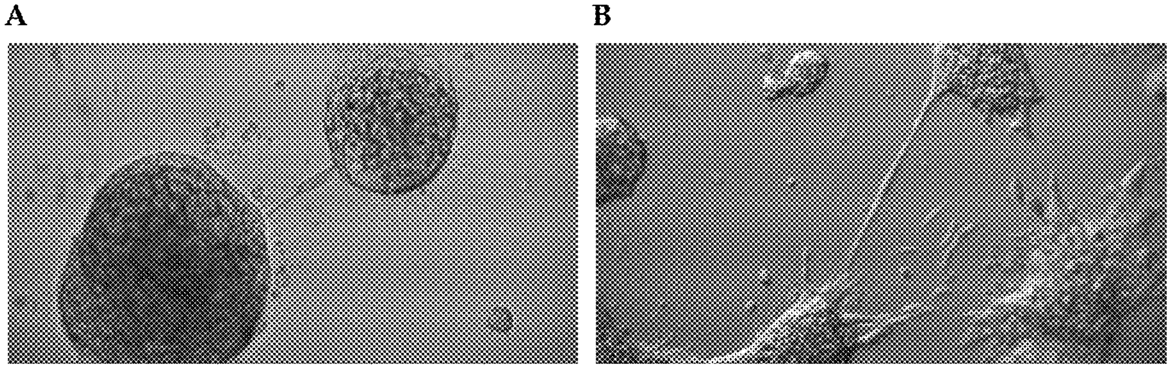
FIG. 2—shows 4T1 cells cultured on a hydrogel, the cells forming three dimensional structures, spheroids. After long term culture, cell migrating between neighbouring spheroids are observed.
Figure 3:
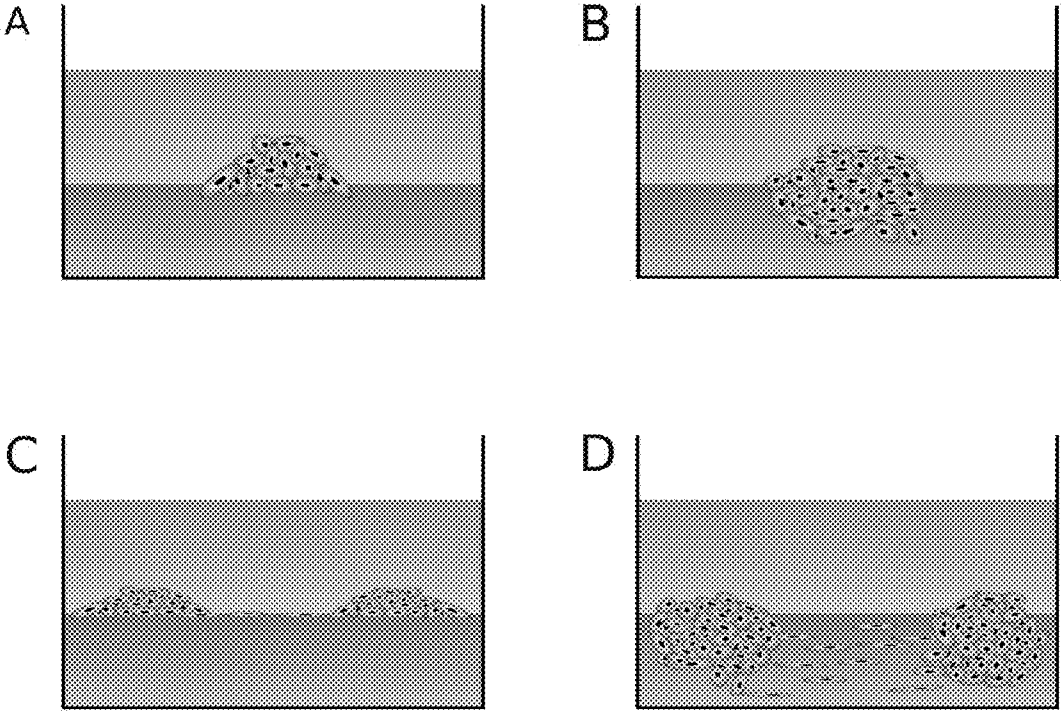
FIG. 3—shows culture wells half-filled with hydrogel and with a culture medium poured into. Various kinds of cell growth and behaviour depending on the hydrogel are illustrated. FIGS. A and C show growth and migration on a hard and thick hydrogel, and FIGS. B and D show growth and migration on a soft and thin hydrogel. FIG. A shows cell growth on the surface of the hydrogel, this being a 3D growth but on the surface of the hydrogel. FIG. B shows cell growth into the inside of the hydrogel. FIG. C shows migration on the surface of the hydrogel. FIG. D shows two lumps, which have grown into the hydrogel, and cells migrating between them inside the hydrogel.

Onto the hydrogel prepared in Example II, neoplastic 4T1 (murine mammary carcinoma) cells were seeded at density of 10 thousand cells/well of a 48-well plate. The cells were cultured in RPMI+10% FBS medium. The result of the experience were spheroids formed by the neoplastic cells (FIG. 2).

Example V

A Comparative Example Using Prior Art Concentrations

Assays were performed, in which hydrogels were produced according to the methods disclosed in the prior art (Bigi et al.). To that end, a hydrogel of a composition 5% type A Bloom 300 gelatin (mass) and GTA of mass concentrations described in Tables 1-8 was prepared. In the experiments shown in Table 1, 2, 3 and 4, the protein hydrogel was dried 24 h (the drying was according to the description in publication Bigi et al.), whereas in Tables 5, 6, 7 and 8, the prepared protein hydrogel was cross-linked 24 h, with A meaning that the hydrogel was not rinsed, B meaning that it was rinsed 5× with $dH_2O$ and C meaning that it was rinsed 5× with PBS. The rinsing steps were not described in the cited publication. After the experiment, the resulting cells were evaluated: 0—no flattened cells; most probably all are dead; 1—a small number of flattened cells present; 2—a high number of flattened cells present. The Tables below show the obtained results.

Seeded Cell Line is: Panc_02

TABLE 1

| GTA concentration [%] | 0.1 | 0.125 | 0.25 | 0.5 |
|---|---|---|---|---|
| A | 0 | 0 | 0 | 0 |
| B | 0 | 0 | 0 | 0 |
| C | 1 | 1 | 0 | 0 |

TABLE 2

| GTA concentration [%] | 1 | 1.5 | 2 | 2.5 |
|---|---|---|---|---|
| A | 0 | 0 | 0 | 0 |
| B | 0 | 0 | 0 | 0 |
| C | 0 | 0 | 0 | 0 |

TABLE 5

| GTA concentration [%] | 0.1 | 0.125 | 0.25 | 0.5 |
|---|---|---|---|---|
| A | 0 | 0 | 0 | 0 |
| B | 0 | 0 | 0 | 0 |
| C | 1 | 1 | 0 | 0 |

TABLE 6

| GTA concentration [%] | 1 | 2 | 3 | 4 |
|---|---|---|---|---|
| A | 0 | 0 | 0 | 0 |
| B | 0 | 0 | 0 | 0 |
| C | 0 | 0 | 0 | 0 |

Seeded Cell Line is: HUVEC

TABLE 3

| GTA concentration [%] | 0.1 | 0.125 | 0.25 | 0.5 |
|---|---|---|---|---|
| A | 0 | 0 | 0 | 0 |
| B | 2 | 2 | 2 | 0 |
| C | 2 | 2 | 2 | 2 |

TABLE 4

| GTA concentration [%] | 1 | 1.5 | 2 | 2.5 |
|---|---|---|---|---|
| A | 0 | 0 | 0 | 0 |
| B | 0 | 0 | 0 | 0 |
| C | 0 | 0 | 0 | 0 |

TABLE 7

| GTA concentration [%] | 0.1 | 0.125 | 0.25 | 0.5 |
|---|---|---|---|---|
| A | 0 | 0 | 0 | 0 |
| B | 1 | 1 | 1 | 0 |
| C | 2 | 1 | 1 | 1 |

TABLE 8

| GTA concentration [%] | 1 | 1.5 | 2 | 2.5 |
|---|---|---|---|---|
| A | 0 | 0 | 0 | 0 |
| B | 0 | 0 | 0 | 0 |
| C | 1 | 1 | 1 | 1 |

The above data show that on the higher concentration hydrogels from the prior art, the cells do not grow or grow flattened. In the case of the HUVEC cell line, it prevents the formation of blood vessels, i.e. the performing of an angiogenesis assay. In the case of the Panc_02 cell line, this means that if the cross-linking agent has been properly removed/neutralised, the cells can grow but the growth is on a hard medium so that the cells flatten as is typical for a standard 2D culture.

Example VI

Production of the Protein Hydrogel with $dH_2O$ Solvent

To produce 50 hydrogel portions (300 μl each) of a concentration of 0.3%, 0.045 g of type A Bloom 300 gelatin was weighed and dissolved in 14.955 ml of $dH_2O$. Each hydrogel portion contained 0.0009 g of gelatin. The solution was heated to 37° C. for 30 minutes to dissolve the gel and then sterilised by filtration. The gel prepared in this manner was pipetted into a 48-well plate, at 300 μl per well. Two portions remained unpipetted for disposal. The 48-well plate with 48 gel portions was put into a fridge to cool and then to stabilise for 23 h in the fridge temperature. By taking 0.0105 mg of GTA and supplementing to 300 μl of $dH_2O$, 0.0035% (mass) GTA solution in $dH_2O$ was prepared earlier and its temperature was reduced to the fridge temperature by allowing it to stand for minimum 30 minutes in the fridge. Onto the surface of a cool, stabilised and gelified gel, 300 μl of a cooled GTA solution was added. The additions of GTA were made on ice. Then the plate with the gel with GTA poured onto was put to the fridge for 72 h. In each hydrogel portion, there was about 0.0105 mg of GTA. After that time, the resulting hydrogel was purified of excess GTA by rinsing the hydrogel 3 times with PBS. The hydrogel prepared in this manner is ready for further use.

Example VII

Hydrogel Production for a Cell Culture without it being Necessary to Carry Out the Step of Removing the Residues of Toxic GTA To produce 50 hydrogel portions (250 μl each) of a concentration of 0.6%, 0.075 g of type A Bloom 300 gelatin was weighed and dissolved in 12.425 ml of PBS. Each hydrogel portion contained 0.0015 g of gelatin. The solution was heated to 37° C. for 30 minutes to dissolve the gel and then sterilised by filtration. The gel prepared in this manner was pipetted into a 48-well plate, at 250 μl per well. 2 portions remained unpipetted for disposal. The 48-well plate with 48 gel portions was put into a fridge to cool and then to stabilise for 60 minutes in the fridge temperature. By taking 0.018 mg of GTA and supplementing to 30 μl of $dH_2O$, 0.06% (mass) GTA solution in $dH_2O$ was prepared earlier and its temperature was reduced to the fridge temperature by allowing it to stand for minimum 30 minutes in the fridge. To a cool, stabilised, but not gelified gel, 30 μl each of a cooled GTA solution was added. The addition of GTA was made on ice. Then the plate with the gel with GTA added was put to the fridge for 72 h. In each hydrogel portion, there was about 0.018 mg of GTA. The hydrogel prepared in this manner is ready for further use.

Example VIII

Production of the Protein Hydrogel with Type B Gelatin

To produce 60 hydrogel portions (250 μl each) of a concentration of 0.4%, 0.06 g of type B gelatin was weighed and dissolved in 14.940 ml of PBS solution. Each hydrogel portion contained 0.001 g of gelatin. The solution was heated to 37° C. for 30 minutes to dissolve the gel and then sterilised by filtration. The gel prepared in this manner was pipetted into a 48-well plate, at 250 μl per well. Twelve portions remained unpipetted for disposal. The 48-well plate with 48 gel portions was put into a fridge to cool and then to stabilise for 50 minutes in the fridge temperature. By taking 0.045 mg of GTA and supplementing to 30 μl of $dH_2O$, 0.15% (mass) GTA solution in $dH_2O$ was prepared earlier and its temperature was reduced to the fridge temperature. To a cool and partially stabilised, but not gelified gel, 30 μl of a cooled GTA solution was added. GTA addition took place on ice. In each protein hydrogel portion, there was about 0.045 mg of GTA. Then the plate with the gel with GTA poured onto was put to the fridge for 72 h. After that time, the resulting protein hydrogel was purified of excess GTA by rinsing the hydrogel 3 times with PBS. The hydrogel prepared in this manner is ready for further use.

Example IX

Reproducibility of Angiogenesis

To produce 50 hydrogel portions (250 μl each) of a concentration of 0.4%, 0.05 g of type A Bloom 300 gelatin was weighed and dissolved in 12.45 ml of PBS. Each hydrogel portion contained 0.001 g of gelatin. The solution was heated to 37° C. for 30 minutes to dissolve the gel and then sterilised by filtration. The gel prepared in this manner was pipetted into a 48-well plate, at 250 μl per well. 2 portions remained unpipetted for disposal. The 48-well plate with 48 gel portions was put into a fridge to cool and then to stabilise for 40 minutes in the fridge temperature. By taking 0.03 mg of GTA and supplementing to 30 μl of $dH_2O$, 0.1% (mass) GTA solution in $dH_2O$ was prepared earlier and its temperature was reduced to the fridge temperature by allowing it to stand for minimum 30 minutes in the fridge. To a cool, stabilised, but not gelified gel, 30 μl each of a cooled GTA solution was added. The additions of GTA were made on ice. Then the plate with the gel with GTA added was put to the fridge for 72 h. In each hydrogel portion, there was about 0.03 mg of GTA. The protein hydrogel prepared in this manner was rinsed 3× with PBS. The protein hydrogel was prepared in 10 separate production batches, in 4 replicates each time.

On the protein hydrogel prepared in this manner, cells were seeded and after 10 h of incubation the cells were observed under microscope. Table 9 below shows the assay results, where:

A—the cells form well-shaped tubes
B—the cells start to form tubes

TABLE 9

| Production | Replicates | | | |
|---|---|---|---|---|
| batch | 1 | 2 | 3 | 4 |
| 1 | A | A | A | A |
| 2 | A | A | A | A |
| 3 | A | A | A | A |
| 4 | A | A | A | B |
| 5 | A | A | A | A |
| 6 | A | A | A | A |
| 7 | A | A | A | A |
| 8 | A | A | A | A |
| 9 | A | A | A | A |
| 10 | B | A | A | A |

The experiment shows that one of the characteristics of the method being the subject matter of the disclosure is a high reproducibility of results. In all 40 attempts, the angiogenesis assay returned a positive result and only twice was slightly delayed in time, which may be due to a statistical error. The above results represent a significant improvement in the effectiveness of the angiogenesis assay as compared to competitive products.

The protein hydrogel being the subject matter of the invention makes it possible to obtain a medium with precisely selected parameters, e.g. density or hardness of the hydrogel. These parameters have an influence on the reproduction of physiological conditions in which the cell grew naturally, which in turn affects their behaviours, such as: migration inside the hydrogel, ability to form spheroids, etc.

The invention claimed is:

1. A method of producing a protein hydrogel comprising reagent A, being gelatin, reagent B, being a cross-linking agent, being GTA, and solvent, the method comprising the steps of:

a) addition a suitable amount of reagent A, in an aqueous solution;
b) heating up the mixture of step a) to dissolve the gel;
c) initially stabilizing the gel;
d) preparing reagent B, by dissolving it in an aqueous solution and cooling it;
e) adding reagent B, as prepared in step d), to the gel prepared in step c);
f) cross-linking;

characterised in that reagent A is present in the final concentration from 0.3% wt. to 0.8% wt., with a ratio of reagent A to reagent B of 0.75-2.4 mg to 0.021-0.045 mg respectively, the initial stabilization of the gel in step c) takes place when the gel reaches the temperature 0° C.-12° C. and its duration is at least about 5 minutes;

steps d)-f) are performed at reduced temperature from about 0° C. to about 12° C., in step f) the duration of cross-linking is at least 12 h.

2. The method according to claim 1, characterized in that the duration of initial stabilization in step c) is 30 minutes to 48 hours.

3. The method according to claim 1, characterized in that the duration of cross-linking is above 48 hours.

4. The method according to claim 1, characterized in that in step a) the aqueous solution is selected from dH2O or PBS.

5. The method according to claim 1, characterized in that the duration of initial stabilization in step c) is 45 minutes to 24 hours.

6. The method according to claim 1, characterized in that the duration of crosslinking is above 72 hours.

7. The method according to claim 1, characterized in that the mixture obtained in step e) is subjected to additional mixing.

8. The method according to claim 1, characterized in that the hydrogel obtained in step f) is purified of an excess of reagent B.

9. The method according to claim 8, characterized in that the purification of the hydrogel takes place by means of rinsing with solvent or by means of neutralizing reagent B.

10. The method according to claim 9, characterized in that the solvent is PBS.

11. The method according to claim 9, characterized in that the neutralization of reagent B is achieved by adding L-lysine.

* * * * *